United States Patent
Meyendorf et al.

(10) Patent No.: US 6,752,023 B1
(45) Date of Patent: Jun. 22, 2004

(54) METHOD AND DEVICE FOR CARRYING OUT THE NONDESTRUCTIVE MATERIAL CHARACTERIZATION OF FERROMAGNETIC SUBSTANCES

(75) Inventors: Norbert Meyendorf, Centerville, OH (US); Henrik Rösner, Saarwellingen (DE); Alexandre Sourkov, Saarbrücken (DE); Fritz Michel, Weissensee (DE)

(73) Assignee: Fraunhofer Gesellschaft zur Forderung der Angewandten Forschung E.V., Munich (DE)

( * ) Notice: Subject to any disclaimer, the term of this patent is extended or adjusted under 35 U.S.C. 154(b) by 151 days.

(21) Appl. No.: 10/089,116

(22) PCT Filed: Jul. 21, 2000

(86) PCT No.: PCT/EP00/06995

§ 371 (c)(1),
(2), (4) Date: Jul. 22, 2002

(87) PCT Pub. No.: WO01/23877

PCT Pub. Date: Apr. 5, 2001

(30) Foreign Application Priority Data

Sep. 27, 1999 (DE) .......................................... 199 46 240

(51) Int. Cl.$^7$ ................................................ G01B 7/16
(52) U.S. Cl. .............................. 73/779; 73/763; 73/774
(58) Field of Search .......................... 73/779, 763, 768, 73/772, 774, 775

(56) References Cited

U.S. PATENT DOCUMENTS 4,408,160 A 10/1983 King et al.
5,166,613 A 11/1992 Perry
5,650,570 A 7/1997 Goto et al.

FOREIGN PATENT DOCUMENTS

| DE | 4343225 C2 | 5/1996 |
| DE | 19631311 A1 | 2/1998 |
| EP | 0683393 A1 | 11/1995 |
| EP | 0704686 A1 | 4/1996 |
| WO | 89/10558 | 11/1989 |
| WO | 98/05976 | 2/1998 |
| WO | 01/23877 A1 | 4/2001 |

*Primary Examiner*—Edward Lefkowitz
*Assistant Examiner*—Corey D. Mack
(74) *Attorney, Agent, or Firm*—Burns, Doane, Swecker & Mathis, L.L.P.

(57) ABSTRACT

Disclosed is a method for the nondestructive metal characterization and the measurement of stress in the interior of a ferromagnetic part under test by means of measuring a high-frequency electric signal caused by flowing an excitation current through the part under test and/or by the mechanical deformation of the part under test.

The present invention is distinguished by the electric potential of the part under test being detected by means of direct or indirect electric tapping on said part under test or a region of said part under test and a high-frequency potential component, which is used as the high-frequency noise signal for determining test parameters, is determined from the electric potential of the part under test caused by changes in magnetization processes.

19 Claims, 4 Drawing Sheets

METHOD AND DEVICE FOR CARRYING OUT THE NONDESTRUCTIVE MATERIAL CHARACTERIZATION OF FERROMAGNETIC SUBSTANCES

FIELD OF THE INVENTION

The present invention relates to a method and a device for carrying out the nondestructive material characterization and the measurement of stress in the interior of a ferromagnetic part under test by measuring the high-frequency change in its electric potential caused by flowing an excitation current through the part under test or by the deformation of the part under test. Furthermore, a purpose of the method is utilizing ferromagnetic reference materials as temperature sensors and gas sensors.

BACKGROUND OF THE INVENTION

Determining the properties of ferromagnetic materials by means of micromagnetic methods is known in the art. The principle of these methods is based on continually changing the magnetic domain structure within the material by subjecting the to-be-examined ferromagnetic material cyclically to an external change in magnetization. Boundaries between regions of the same magnetization, so-called Bloch walls, are moved through the structure of the material which for their part interact with the microstructure of the material. Such interaction can be received as electromagnetic signals, known as Barkhausen noise in the literature. Evaluation of these signals, representing Barkhausen noise, can provide information about the microstructure of the material and the stress in its interior. The published publications DE 43 43 225 C 1, EP 683393 A1 and DE 196 31 311 C2 describe such methods for nondestructive testing of ferromagnetic substances which permit determining material properties such as grain structure and internal stress.

Such micromagnetic interaction can also be determined by measuring superimposed permeability, analysis of harmonic waves as well as dynamic magnetostriction.

Devices based on these micromagnetic processes have been developed and applied. A cyclic magnetic field is generated in an as such known manner via an electromagnet and the Barkhausen noise is received with the aid of a magnetic inductive sensor on the surface of the to-be-tested part. In addition to this, a Hall probe is required to measure and control the cycle period of the bias magnetic field strength (cf. DE 43 43 225 C2). Only the analysis of harmonic waves does not require using magnetically inductive sensors. A simplification of the device for measuring micromagnetic test parameters is realized in DE 196 31 311 C2. As changes in magnetization processes are excited by current flowing through and a measure of the excitation is the time-dependent course of the current strength, an electromagnet and a Hall probe are no longer required. The device comprises only two electrodes and a magnetically inductive sensor. In this manner, a fixed sensor geometry comprising an electrogmagnet respectively two current electrodes and a sensor element is always given. However, such given fixed geometry greatly restricts the possible utilization of such a measuring device.

All generic methods known in the art have the drawback that at least one magnetically inductive sensor or a Hall probe is required, which for example must be placed at the measuring position on a part under test. However, the hitherto known test methods have failed at inaccessible points, at high temperatures or in difficult environmental conditions.

WO89/10556 deals with a process for determining mechanical stress in the interior of ferromagnetic objects. It is used for detecting Barkhausen noise by means of wire strain gauges which must be attached to the to-be-examined object in a suited manner dependent on its geometry. In particular, the known method cannot be used on object surfaces which are unsuited for such attachment of wire strain gauges, for instance if their surface temperatures are too high.

SUMMARY OF THE INVENTION

The object of the present invention is to further develop a method and a device for the nondestructive material characterization and the measurement of stress in the interior of a ferromagnetic part under test by flowing an excitation current through the part under test or by the deformation of the part under test caused by the high-frequency change in its electric potential in such a manner that the previously mentioned disadvantages of the prior art are avoided. In particular, the object is to expand the possibilities of the method with regard to the versatility of its application. Possibilities are to be created to also be able to apply the method for determining the temperature and/or the gas composition respectively the chemical activity of certain process gas compositions.

The solution to the object of the present invention is given in claim 1. An invented device for carrying out the invented process is the subject matter of claim 16. Advantageous further developing features of the inventive idea are the subject matter of the subclaims as well as the description and the accompanying drawings. An element of the present invention is that a generic method according to the introductory part of claim 1 is further developed in such a matter that the electric potential of the part under test is determined by direct or indirect electrical tapping of the part under test, that the high-frequency potential component caused by a change in magnetization is determined from the electric potential of the part under test and is utilized as the high-frequency noise signal for determining the test parameters.

An essential aspect of the invented process is obviation of all magnetically inductive sensors, Hall probes or electromagnets which must be positioned on respectively relative to the part under test, thereby, on the one hand, considerably reducing the technical complexity and, on the other hand, creating significant advantages regarding possible applications of this method. Obviation of positioning sensors in relation to the part under test at the same time also eliminates the significance of the lift-off sensitivity of the sensors during measuring. With the invented method, the measuring results are less subject to disturbing influences and are therefore more accurate, because, as will be described in more detail below, only the potential and the current strength are measured. By this means, determination of the micromagnetic test parameters becomes largely independent of sensors respectively independent of measuring devices. Furthermore, the micromagnetic test parameters can be determined integrally over large regions of the part under test. However, at the same time, the method also permits determining the micromagnetic test parameters with high local resolution and direction dependent. Finally, the invented method permits utilizing ferromagnetic reference materials, in particular in difficult environmental conditions, for example lack of space respectively lack of accessibility, high temperatures and corrosive media.

Measuring the potential on the part under test occurs with the aid of two electrodes which are contacted with the part under test and form with it a closed electric circuit, in which a current source is provided. Depending on the magnetic behavior of the to-be-examined material and its cross section area, a cyclical current strength is selected in such a manner that a ferromagnetic hysteresis occurring in the to-be-examined material can be measured. Preferably the electric current density should be set so high at least locally in the test region of interest that changes in magnetization processes are triggered by means of which the to-be-detected potential noise or Barkhausen noise is generated. In principle, excitation of the ferromagnetic potential noise can also occur by means of mechanical stress or a combination of flowing current through and mechanical stress.

In order to determine the ferromagnetic potential noise, potential tapping is conducted preferably on both sides of the test region. In the case of excitation of the part under test with an alternating current, alternating voltage corresponding to the excitation current frequency, the so-called macropotential which is superimposed on the ferromagnetic potential noise is filtered out with a suited frequency filter. In this manner, a high-frequency noise signal having an amplitude in the $_\mu$V range is obtained and is evaluated correspondingly. The gained noise voltage is material specific and dependent on the interaction of the Bloch wall structure and the microstructure of the material.

Potential tapping at the part under test by means of which the ferromagnetic potential noise is obtained can be measured both in the current flow direction and perpendicular to the current flow direction as well as in the directions in-between.

The frequency of the electric current strength, the so-called excitation frequency, can be selected upwards into the kHz range, because the impedance of the electric current circuit is low. Excitation frequencies in the kHz range permit measuring higher signal amplitudes of the ferromagnetic potential noise and by means of averaging the measured signals over a plurality of periods of the excitation current strength (e.g. 200 periods) makes short measuring times possible.

With an increasing excitation frequency, it is to be expected that, due to resonance effects of the interaction of the excitation current and the Bloch wall structure, increasingly larger noise amplitudes can be measured. Large and lower frequency Bloch wall jumps are to be expected. From a material-dependent cutoff frequency, it is expected that changes in magnetization processes can no longer be excited.

In addition to the excitation frequency, the ferromagnetic potential noise is also dependent on material volume via which potential tapping occurs. A large noise amplitude can be measured with an increasing material volume which is excited to irreversible changes in magnetization processes. In this case, measuring the ferromagnetic potential noise yields integral test parameters.

On the other hand, a small distance between the electrodes for the potential tapping yields a local resolution which is only limited by the noise behavior of the input amplifier.

Of great significance is that in the entire current circuit, only the to-be-examined part under test is ferromagnetic or that at least such a high current density is applied only in the part under test that irreversible changes in magnetization processes are triggered there. Electric lines to the part under test and the electrodes for current impression should preferably be made of nonferromagnetic materials.

Suited signal processing is required for measuring and evaluating the signals. The measured electric macropotential having the superimposed high-frequency noise voltage first passes through a high-pass filter to filter out the low-frequency macropotential and through a preamplifier. With the aid of rectification, frequency filtering, booster amplification and low-pass filtering (signal demodulation), the envelope of the high-frequency noise voltage can be obtained. Plotting these signals with the momentary current strength yields so-called noise profile curves. Using these curves, different test parameters, such as for example the maximum noise amplitude or the position of the maximum noise amplitude with the corresponding current strength can be defined.

Other test parameters can also be defined using the amplified high-frequency signals of the ferromagnetic potential noise, such as for example amplitude distribution spectra or intervals between the noise peaks. In many applications, the test parameter cycle versus the excitation frequency or the amplitude of the current strength (run-up curves) can also be utilized as characteristic measuring curves.

Moreover, it should be demonstrated with reference to the following drawings and preferred embodiments that, apart from material characterization, the invented method is also suited for process control in thermochemical heat treatment as well as a stretch and temperature sensor as well as for detection of microstructural changes in the tips of cracks.

BRIEF DESCRIPTION OF THE DRAWINGS

The present invention is made more apparent in the following using preferred embodiments with reference to the accompanying drawings by way of example without the intention of limiting the overall inventive idea.

DETAILED DESCRIPTION OF THE INVENTION

Figure 1:
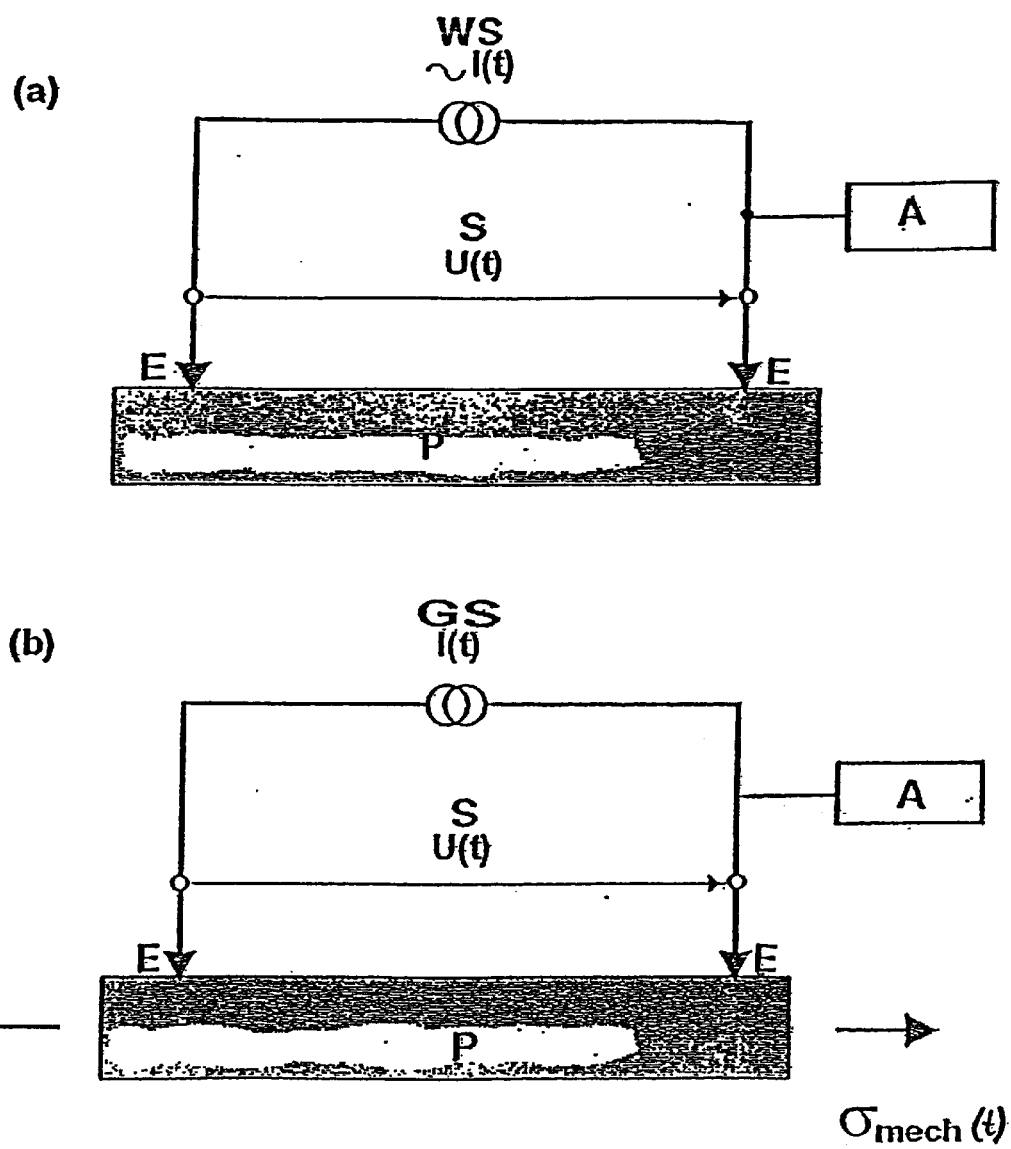
FIGS. 1a, b show a diagram of a basic arrangement for the detection of the ferromagnetic potential noise, FIGS. 2a, b show a current strength versus noise potential diagram and a noise profile curve

FIG. 1 shows a schematic measurement arrangement for detecting the ferromagnetic potential noise in a part under test P, which is connected to an alternating current source WS via two electrodes E. The contacting points of the electrodes E on the part under test P can be randomly selected. However, the arrangement of the electrodes can limit the measuring region inside the part under test P.

At the same time, the purpose of the contacting points of the electrodes E is also tapping the electric potential, which is detected with the aid of a voltage measuring arrangement S. Determining the ferromagnetic potential noise superimposed over the macropotential requires both electric filtering and voltage amplification, which are conducted within the scope of an evaluation unit A.

As an alternative to current excitation as shown in the preferred embodiment according to FIG. 1a, in principle ferromagnetic potential noise can also be obtained by means of preferably cyclically occurring mechanical deformation $\sigma_{mech}(t)$ of the part under test P. This is depicted in FIG. 1b.

The mechanical deformation $\sigma_{mech}(t)$, which is not constant in time, can be carried out in conjunction with a current excitation by means of a direct current source GS.

Figure 2:
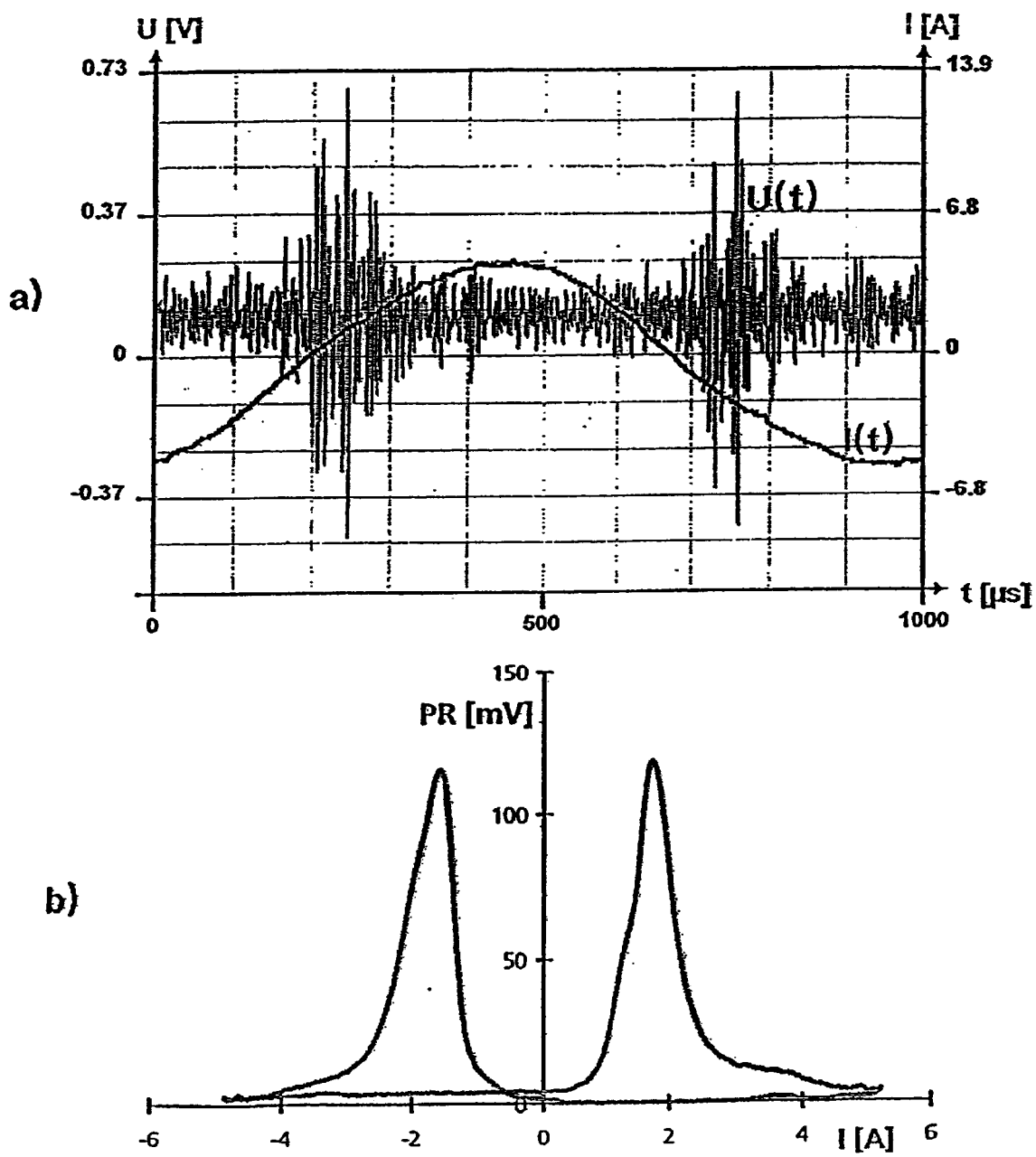

The high-frequency noise signal, which usually is provided with a signal amplitude in the $_\mu V$ range and is amplified for further signal processing, is obtained by means of frequency filtering, which usually occurs within the scope of the evaluation unit A. In a time versus voltage and time versus current strength diagram, FIG. 2a shows the time-dependent current strength I(t) in relation to the amplified high-frequency signal of the ferromagnetic potential noise U(t). The characteristic measuring courses of both function cycles permit generating characterizing noise profile curves PR(I) for material selection, as will be shown further on. FIG. 2b depicts such a noise profile curve PR(I).

Figure 3:
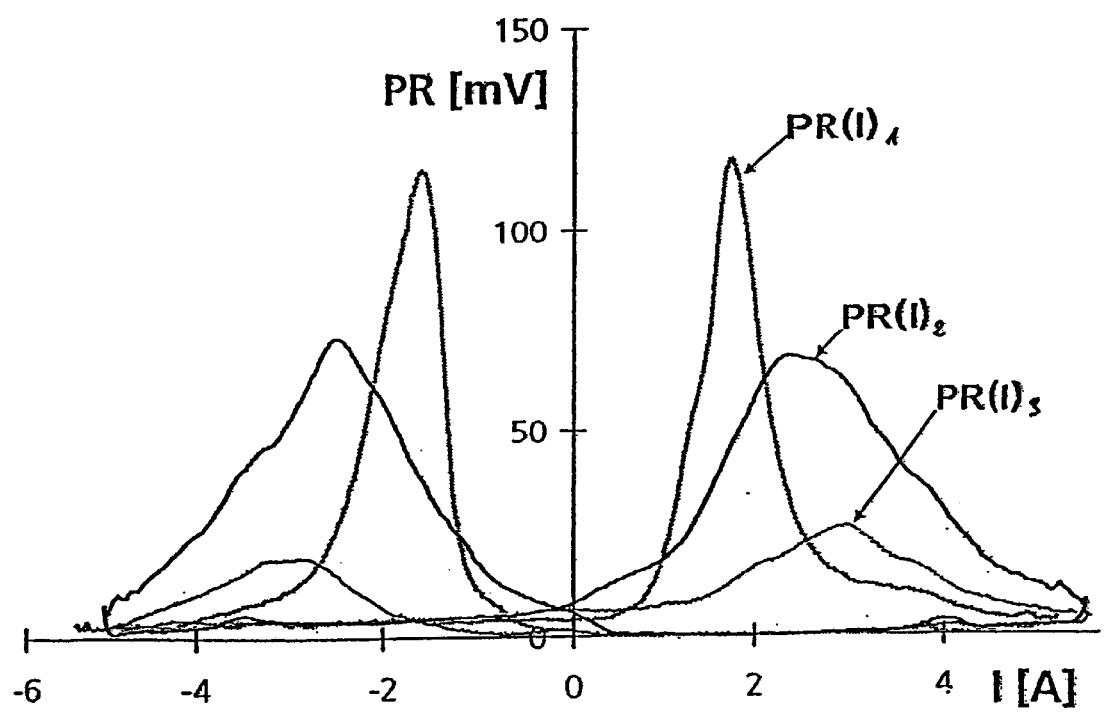
FIG. 3 shows noise profile curves measured on different steel qualities

FIG. 3 shows different noise profiles $PR(I)_1$, $PR(I)_2$, $PR(I)_3$ measured on round specimens (diameter=2 mm, length=25 mm) of different steel quality. With an increasing magnetic respectively mechanical hardness of the materials, a reduction in amplitude of the ferromagnetic potential noise and a shift in predominant noise activity to higher current strengths can be seen. $PR(I)_1$ represents the noise profile curve of welding wire, $PR(I)_2$ of fine grain construction steel and $PR(I)_3$ of hardened steel.

Moreover, with the aid of this described dependency of the noise profile curves of the used materials, process control can be conducted during thermochemical heat treatment of steels and similar materials.

In conventional hardening furnaces, usually oxygen probes are used in process controls. The activity of the carbon atmosphere is determined by measuring the oxygen partial pressure (Boudouard equilibrium). In order to ensure the thermochemical heat treatment in vacuum furncaes, conventional oxygen probes however cannot be used due to the prevailing vacuum. As heat treatment is subject to fluctuations due to, e.g. the furnace leakage, and in certain circumstances quality cannot always be ensured, it is desirable to monitor the furnace atmosphere in vacuum furnaces as well. The hardening activity of the furnace atmosphere is dependent on the concentration of the furnace gas, the temperature and the flow conditions.

Although there are already methods of monitoring such processes on the part under test based on a eddy current test (cf. H. Klümper, Westkamp, F. Hoffmann, P. Mayr: Hochtemperaturbeständige Wirbelstromsensoren zur Charakterisierung des Werkstoffzustandes wahrend der Wärmebehandlung von Stahl; Stiftung Institut for Werkstoftechnik, Bremen Tagungbandbeitrag DGZFP, Dresden, Jahrestagung (1997), application of these methods has hitherto not found as great widespread use as oxygen probes in conventional furnaces, because some problems can crop up. The sensor setup is complicated, because the measurements in the furnace chamber have to be carried out at high temperatures, at about 930° C. Moreover, frequently the sensors have to be adapted to new parts under test. Furthermore, the sensors may falsify the hardening conditions at the measuring site, because the measurement has to be conducted on the component and the gas flow conditions at the measuring site therefore change.

Figure 4:
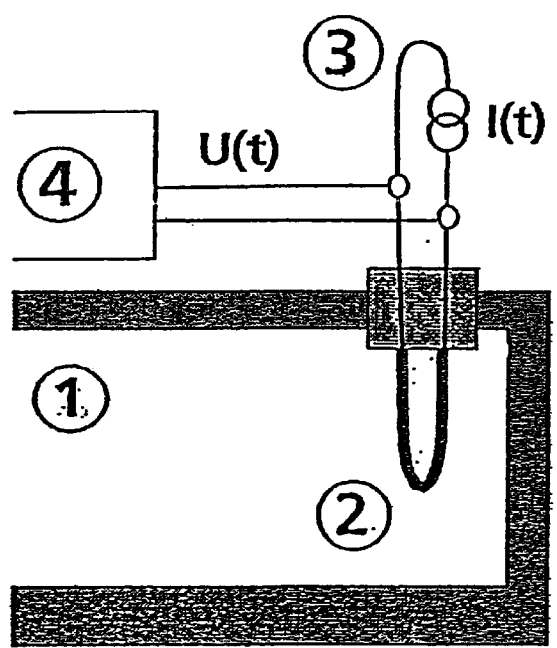
FIG. 4 shows the principle setup of a sensor for monitoring the atmospheric activity in industrial furnaces.

According to the present invention, process monitoring in vacuum furnaces can be realized by means of measuring the ferromagnetic potential noise on a ferromagnetic reference material. The method is based on exposing this reference material to the furnace atmosphere and monitoring the magnetic properties of the reference material from outside the furnace. The reference material changes its chemism and material properties during the process due to the diffusion processes. A characteristic change in magnetic properties during the process is therefore a measure of the activity of the furnace atmosphere. It is important to ensure that the reference material has a sufficiently high Curie point. The basic setup of such an arrangement is shown in FIG. 4.

A predetermined furnace atmosphere, into which a replaceable reference wire 2 projects as the part under test develops in a process furnace 1. All the components 3 required for determining the measured values, such as electric lines for the current flowing through the reference wire 2 and for the potential tapping are located outside the furnace 1. A signal evaluation unit 4 provides the corresponding monitoring and determination of the furnace atmosphere conditions.

The advantages of the use of the invented method of determining the process atmosphere inside industrial furnaces is that measuring can occur on line and the flow conditions are not falsified by a sensor that would otherwise be required.

Moreover, the micromagnetic test parameters are tension-sensitive and are utilized in practice for measuring tension and stress in the interior. The ferromagnetic potential noise can also be utilized for measuring tension and stress in the interior. As the magnetic properties of a wire can be measured at the ends of the wire, ferromagnetic reference materials can be utilized for measuring stretching. Therefore, wire strain gauges which utilize magnetic properties to measure strain are feasible.

Tension-sensitive respectively deformation-sensitive ferromagnetic fibers or wires can be embedded in structures made of synthetic materials, glasses, building materials and composite materials in order to monitor stress in the interior or deformation.

Use of ferromagnetic reference materials can also be utilized for sensitive temperature measurement at inaccessible points or in difficult environmental conditions. The ferromagnetic properties are especially sensitive to temperature just below the Curie point and drop steeply at temperatures near the Curie point. In this temperature range, the ferromagnetic order is destroyed by the temperature. A prerequisite is that the measurement range is selected below the Curie point.

A plurality of reference materials with different Curie points are at disposal so that use in different temperature ranges is possible. For example, cobalt has a Curie point of about 1120° C. and the alloy bearing the trade name Chronoperm one of 180° C.

Another possible application of the invented method is detection of microstructural changes at tips of cracks in parts under test. A method to describe the ductile fracture behavior of materials and derive corresponding materials is based on the so-called J-integral concept. The plotting of crack resistance curves® curves) required for this purpose occurs on specimen bodies especially provided with a fatigue crack. The accuracy of the mechanical fracturing characteristic values determined therefrom depends decisively on monitoring of the micromechanical process at the crack tip during the application of stress on the specimen. Visual observation of these processes is usually not possible, because these processes begin in the middle of the inaccessible crack front. Crack tip processes, stretch zone formation, hollow space formation, crack initiation, crack progression—are linked to the characteristic signal times of the electromagnetic potential noise dependent on material composition and grain structure formation.

Figure 5:
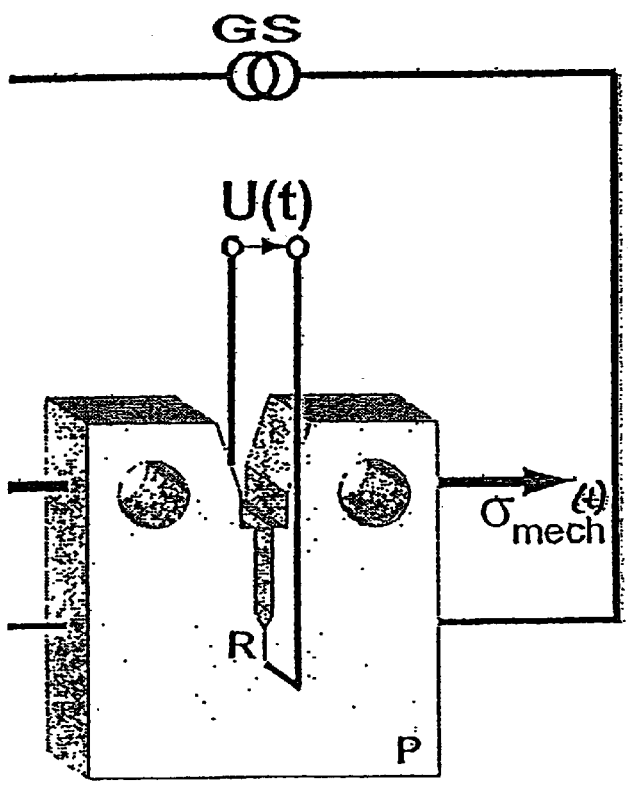
FIG. 5 shows the principal setup for the use of the potential noise to control crack initiation and crack progression in fracture mechanics specimens.

Advantages of the use of potential noises in plotting crack resistance curves are high attainable accuracy and lower costs for conducting the tests. Moreover, the potential noise can also be used in a simple manner for monitoring the development of known cracks in components in the sense of risk prediction. FIG. 5 shows a basic setup for use of the potential noise for controlling crack initiation and crack progression on fracture mechanics specimens. The part under test P provided with crack R is flowed through with a direct current I in the described manner. The part under test itself experiences a mechanical stress of $\sigma_{mech}(t)$, which is not constant in time. Tapping for potential examination U(t), which yields high resolution information about further crack progression, occurs directly at the site of crack formation R.

List of references
P part under test
E electrodes
WS alternating current source
GS direct current source
S voltage measuring arrangement
R crack
A evaluation unit
1 industrial furnace
2 reference wire
3 reference wire holder with electric lines for flowing current through and potential tapping
4 signal evaluation unit

What is claimed is:

1. A method for nondestructive metal characterization and measurement of stress in the interior of a ferromagnetic part under test by means of measuring a high-frequency electric signal induced by an excitation current flowing through the part under test and/or by the mechanical deformation of said part under test, wherein;
    an electric potential of said part under test is detected by means of direct or indirect electric tapping on said part under test or on a region of said part under test; and
    a high-frequency potential component, which is used as a high-frequency noise signal for determining test parameters, is determined from said electric potential of said part under test caused by changes in magnetization processes that are induced by the excitation current and/or by the mechanical deformation.

2. The method according to claim 1, wherein alternating current is employed for flowing current through said part under test, preferably with frequencies from several Hertz to several kHz.

3. The method according to claim 1,
    wherein said potential tapping on said part under test occurs during flowing an excitation current through in the current flow direction or random direction or at random site in the current circuit.

4. The method according to claim 1,
    wherein the macropotential coming from the excitation current is suppressed in the potential signal tapped on said part under test so that only the remaining higher frequency potential component forming the noise signal is evaluated.

5. The method according to claim 2,
    wherein in evaluating said noise signal, a plurality, preferably several hundred, periods of excitation current of the time-dependent and current-strength-dependent signal is averaged.

6. The method according to claim 1,
    wherein the current density during flowing current through said part under test is selected in such a manner that irreversible changes in magnetization processes are triggered in said part under test.

7. The method according to claim 1, wherein, by means of signal processing, such as filtering, rectification and amplification, an envelope of said high-frequency noise signal is generated which, plotted versus the excitation current strength, yields a noise profile curve on the basis of which test parameters and material properties or interior stress derived therefrom are obtained.

8. The method according to claim 1,
    wherein a phase analysis occurs between the excitation current respectively the mechanical stress and the noise signal setting in.

9. The method according to claim 1,
    wherein direct current is used for flowing current through said part under test and said part under test is exposed once or cyclically to successive mechanical stress.

10. The method according to claim 1, wherein thermal and/or mechanically induced deformations or internal stress inside said part under test are detected.

11. The method according to claim 1, wherein said part under test is fixed as a sensor in a carrier material in order to determine its deformation or tension state by evaluating the noise signal generated by said part under test.

12. The method according to claim 1, which comprises monitoring thermochemical heat treatment of goods.

13. The method according to claim 12, wherein said part under test is exposed to an atmosphere inside a hardening, vacuum or sintering furnace and the noise signals provide information about the chemical and thermal conditions inside the furnace atmosphere.

14. The method according to claim 1, which comprises monitoring plastic deformation, crack initiation and crack progression in said part, wherein as a consequence of mechanical stress on said part, preferably at a tip of a crack, the noise signal is utilized for local material characterization and for determining the point of crack initiation in mechanical fracturing testing.

15. The method according to claim 1, which comprises monitoring crack initiation and crack progression in said part wherein the noise signal is utilized for continuous monitoring of crack progression and for monitoring longevity of said part with a risk of fracturing.

16. A device for the nondestructive material characterization of a ferromagnetic part under test utilizing changes in magnetization processes occurring in said part under test, wherein, by means of said measuring device, said part under test is impinged with an excitation current of sufficient strength by means of two electrodes in such a manner that said part under test is locally or entirely premagnetized in such a manner that changing said excitation current and/or the mechanical stress triggers changes in magnetization and the potential noise related thereto is tapped at two further electrodes, detected by an evaluation unit and separated from the superimposed potential caused by said excitation current.

17. The device according to claim 16,
    wherein the electrodes by means of which said excitation current is entered and the electrodes with which the potential of said part under test is tapped are identical.

18. The device according to claim 16,
    wherein said evaluation unit is provided with an amplifier, a frequency filter and/or a rectifier.

19. The device according to claim 16,
    wherein a depiction unit is provided with which the gained noise signal can be depicted graphically and can be interpreted.

* * * * *